Figure 1:
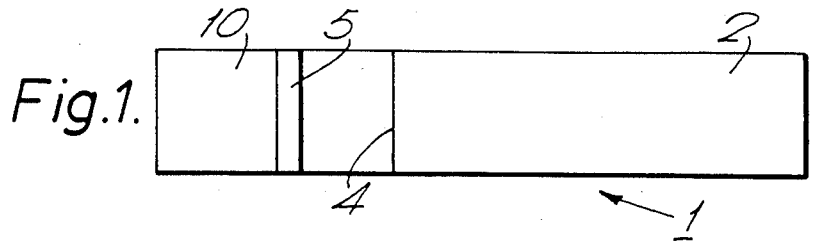
Figure 2:
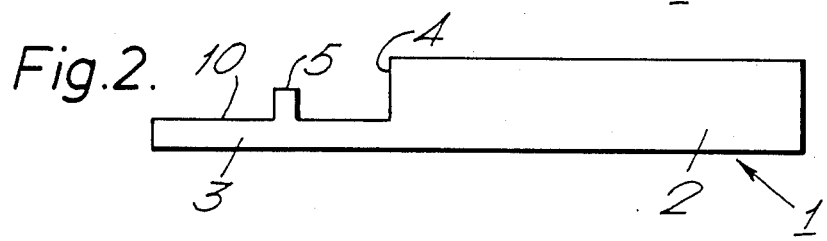
Figure 3:
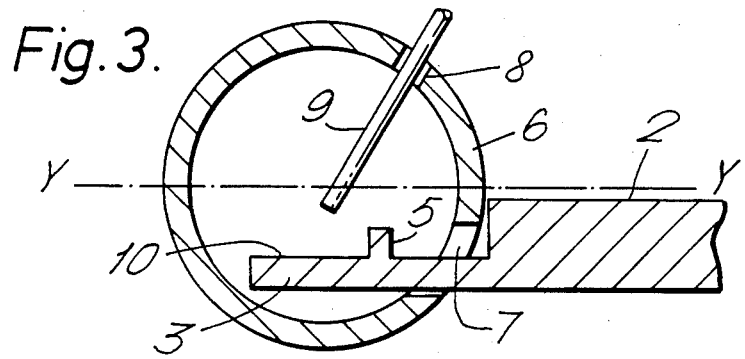
Figure 4:
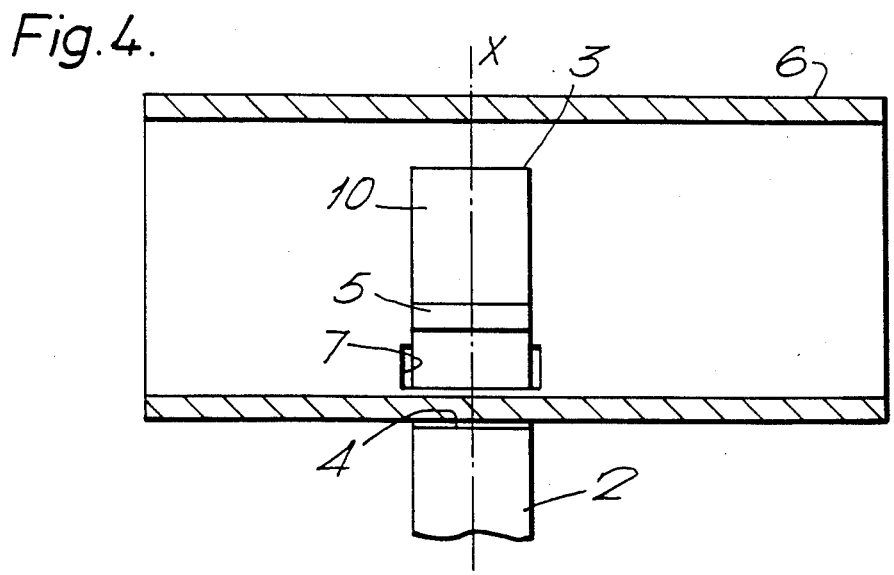
Figure 5:
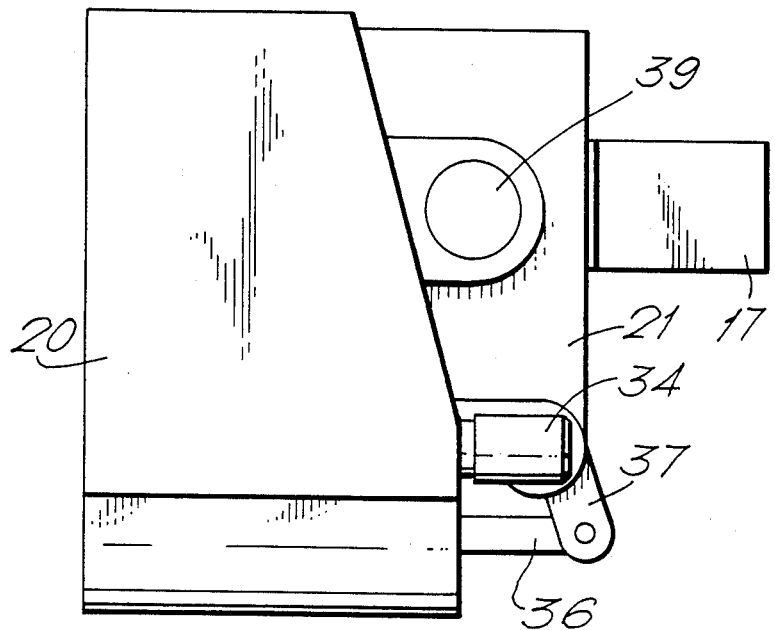
Figure 6:
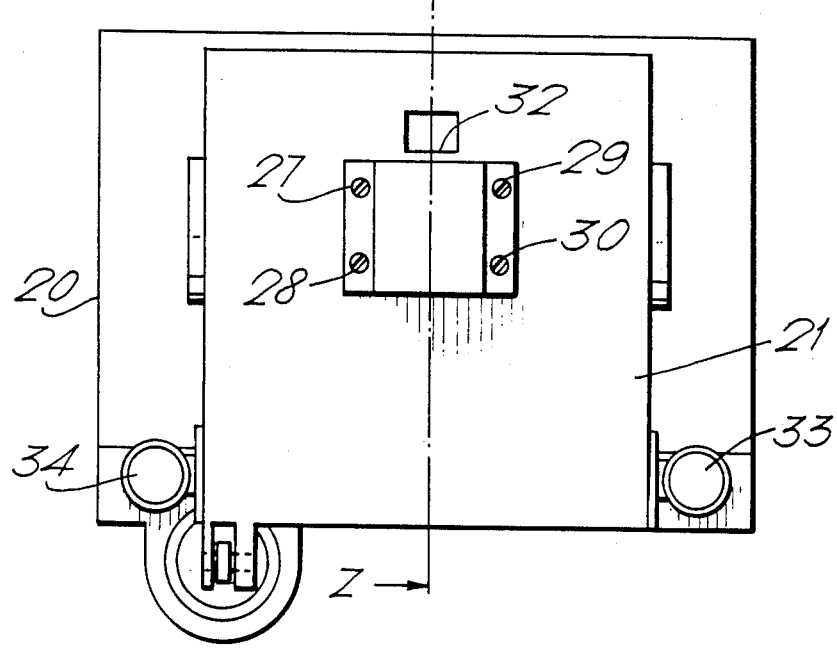
Figure 7:
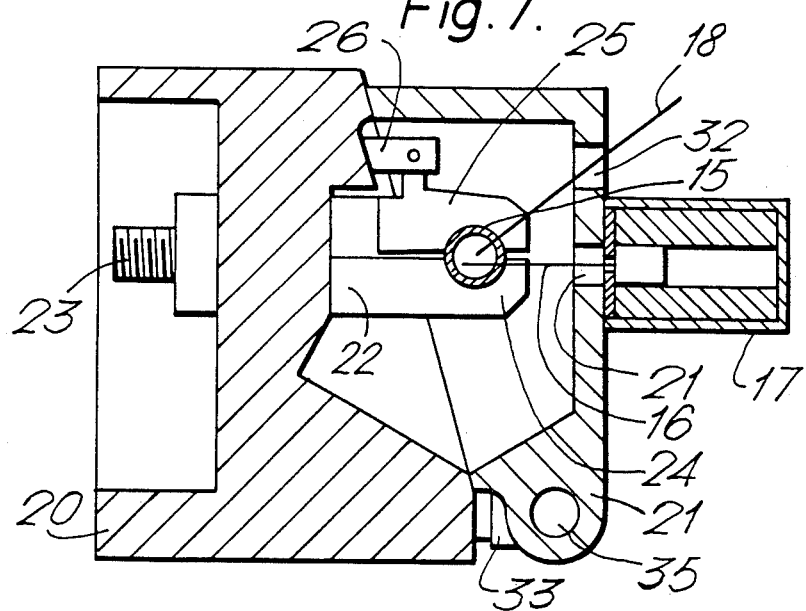

United States Patent [19]
Brown

[11] Patent Number: 4,721,387
[45] Date of Patent: Jan. 26, 1988

[54] GRAPHITE PROBE AND ELECTROTHERMAL ATOMIZER INCLUDING SUCH A PROBE

[75] Inventor: Alistair A. Brown, Linton, England

[73] Assignee: U.S. Philips Corporation, New York, N.Y.

[21] Appl. No.: 927,784

[22] Filed: Nov. 5, 1986

[30] Foreign Application Priority Data

Nov. 12, 1985 [GB] United Kingdom ............... 8527865

[51] Int. Cl.⁴ ........................................... G01N 21/74
[52] U.S. Cl. ..................................... 356/312; 356/244
[58] Field of Search ................................ 356/312, 244

[56] References Cited

U.S. PATENT DOCUMENTS

4,639,136 1/1987 Morton ............................... 356/312
4,657,389 4/1987 Littlejohn .......................... 356/312

FOREIGN PATENT DOCUMENTS

2152234 7/1985 United Kingdom ............... 356/312

Primary Examiner—F. L. Evans
Attorney, Agent, or Firm—Paul R. Miller

[57] ABSTRACT

A graphite probe for an electrothermal atomizer comprises a thick stem portion (3) carrying a thin head portion (2) which meets the stem portion (3) at a step (4) which, in operation, is located outside a cuvette (6) adjacent to a slot (7) through which the probe head (2) is inserted into the cuvette (6). A sample deposition aperture (8) is provided in the cuvette (6) through which a sample can be deposited via a dosing tube (9) on a part (10) of the head portion (2) of the probe. The part (10) of the head portion (2) is separated from the rest of the probe by a ridge (5) which extends across the width of the head (2). The ridge (5) prevents liquid samples having a low surface tension from spreading towards the step (4) and has a mass such that its temperature increase matches that of the rest of the head portion (2) thus reducing the production of double peaks in the measured absorption.

7 Claims, 7 Drawing Figures

GRAPHITE PROBE AND ELECTROTHERMAL ATOMIZER INCLUDING SUCH A PROBE

The invention relates to a graphite probe for an electrothermal atomiser, the probe comprising a stem portion and a head portion.

The invention further relates to an electrothermal atomiser for a spectrophotometer, said atomiser comprising a hollow body of electrically conductive material, means for inserting a probe into the interior of the hollow body, and means for passing an electrical current through the body to heat the interior of the hollow body to a temperature which is sufficient to atomise a sample deposited on the probe wherein the probe comprises a stem portion and a head portion for receiving the sample.

Such a probe and atomiser have been disclosed in UK Patent Application No. 2136144A. In this atomiser the probe was formed of pyrolytic graphite as was the preferred form of hollow body (or cuvette). An atomiser as set forth in the second paragraph has also been disclosed in UK Patent Application No. 2088582A in which the probe (or sample carrier) is formed of graphite of unspecified type. UK Patent Application No. 2071845 discloses such an atomiser in which the probe is in the form of a wire (tungsten) filament. UK Patent Application No. 2113128A discloses a probe made from glassy carbon.

It has been found that probes made from pyroltic graphite and glassy carbon and probes coated with pyrolytic graphite suffer from the disadvantage of sample spreading when samples contain more than about 0.5% v/v of nitric acid. The reduced surface tension of such solutions causes the sample to spread irreproducibly up the probe stem during the drying phase. Various proposals have been made in an attempt to overcome this problem. Initial experiments were conducted with the probe inserted into the cuvette through a slot in the wall in a manner as described in UK Patent Application No. 2136144A. With this configuration only the probe head is heated significantly during the drying phase, while the stem, outside the cuvette, remains cool. It was thought that the sharp temperature gradient along the probe could be responsible for the spreading phenomenon, as the liquid sample would tend to travel to the cooler region outside the cuvette.

An alternative configuration, the 'end entry' probe, allows the probe to enter the cuvette parallel to its long axis. It is, therefore, no longer necessary to cut a slot in the cuvette, and so improved cuvette lifetimes and sensitivity would be expected. The temperature gradient along the probe would now also be much less steep, as a large part of the stem as well as the head would be heated. It was throught that the spreading problem would therefore be alleviated, and that even if some spreading did occur, as much more of the probe stem would be introduced into the hot zone during the atomisation phase, the effects might be less significant.

Such an arrangement was tried and initial results using glassy carbon probes with a pyrolytic graphite coating were promising. However on repeating the measurement it was found that the performance deteriorated until there was no significant improvement in controlling sample spreading over the front entry system.

Other approaches tried were to use microporous glassy carbon probes with either the head or the stem pyrolytically coated. It was found that coating the head and leaving the stem uncoated gave no significant advantage over a fully coated probe while coating the stem and leaving the head uncoated gave a worse performance.

A further approach attempted was to deposit the sample onto a hot probe. However, with the arrangement used in which the probe is heated by the cuvette it was not found to be practicable as the sample boiled inside the pipette before it could be deposited on the probe. It is considered, however, that this arrangement could be advantageous if the probe is heated independently of the cuvette.

A further alternative which has been tried experimentally is to provide a probe in which the stem is thicker than the head, a step being formed where the head and stem meet. The purpose of the step is to prevent the liquid spreading up the stem. This was found to have certain disadvantages. If the step was located outside the cuvette then sample spread as far as the step and a proportion of the sample was then atomised outside the cuvette causing a reduction in sensitivity. Alternatively, if the step was located within the cuvette a double peak was obtained. This is thought to be caused by the different masses of the head and stem which results in the head reaching the atomising temperature before the stem. Consequently the sample which has spread to the step is atomised later than that on the portion of the head remote from the step.

All these attempts at solving the problem of sample spreading have proved unsuccessful and appear to make the use of probe atomisation unsatisfactory for all but a minority of practical samples.

It is an object of the invention to enable the provision of an electrothermal atomiser in which the sample is atomised off a probe inserted into a hollow body which is capable of handling acid samples.

The invention provides graphite probe for an electrothermal atomiser as set forth in the opening paragraph characterised in that the head portion is provided with a ridge which is dimensioned and positioned to have a heating rate similar to that of the rest of the probe head and to provide a barrier impeding the spead of liquid samples from the head to the stem when the probe head is heated within an atomiser.

By forming a ridge which is of comparatively low mass similar to that of the rest of the head portion the problems of double peaks and of sample spreading can both be reduced. If the ridge is perfectly thermally matched to the rest of the probe head then no double peaks will be produced since the ridge temperature profile will exactly match that of the rest of the head and all the sample will be atomised simultaneously. The temperature of the head portion of the probe is raised to the atomising temperature principally by the radiation from the wall of the hollow body or cuvette.

The stem thickness may be greater than the head thickness. This enables a more robust construction of probe.

The stem thickness may be greater than the head plus ridge thickness. This has the advantage that when a front entry atomiser is used the increased thickness stem can be used to close the slot in the tube wall.

The invention further provides an electrothermal atomiser as set forth in the second paragraph characterised in that the head portion is provided with a ridge which is dimensioned to have a heating rate similar to that of the rest of the probe head and to provide a barrier impeding the spread of liquid samples from the head to the stem when the probe is heated within the hollow body and that the probe insertion means is arranged to insert the probe so that the ridge is located within the hollow body.

Such an atomiser enables the advantages of probe atomisation to be obtained while reducing the problems associated with probe atomisation of samples in liquids having a low surface tension, i.e. sample spreading or the production of double peaks.

Embodiments of the invention will now be described, by way of example, with reference to the accompanying drawings, in which:

FIG. 1 shows a plan view of a graphite probe according to the invention,

FIG. 2 is a side elevation of the graphite probe shown in FIG. 1,

FIG. 3 is a cross-sectional view on line X—X of FIG. 4 of the graphite probe of FIG. 2 inserted in a tubular graphite cuvette, FIG. 4 is a cross-sectional view on line Y—Y of FIG. 3 of the graphite probe of FIG. 1 inserted in a tubular graphite cuvette, FIG. 5 is a side elevation of an electrothermal atomiser according to the invention, FIG. 6 is a front elevation of the electrothermal atomiser shown in FIG. 5, and FIG. 7 is a cross-sectional view on line Z—Z of FIG. 6.

FIGS. 1 and 2 show plan and side elevations of a probe 1 having a stem portion 2 and a head portion 3. The stem portion 2 is thicker than the head portion 3 and the stem and head portions meet in a step 4. The head portion 3 is provided with a ridge 5 extending upwardly from its surface when in use. The ridge 5 extends across the full width of the head portion in the embodiment shown but is merely required to extend over such a width as is necessary to effectively prevent the sample from spreading further along the head portion towards the step 4. The size and shape of the ridge 5 are chosen so that the ridge forms an effective barrier to the spread of liquid sample but retains a low mass so that it heats at the same rate as the rest of the probe head when the probe is inserted into the hollow body.

FIGS. 3 and 4 show the probe head 3 inserted in a cuvette 6 which is a tubular graphite body provided with a slot 7 through which the probe is inserted and an aperture 8 through which a sample may be deposited on the probe head 3 either manually with a micro pipette or automatically with an autosampler through a tube 9. The tube 9 is inserted through the aperture 8 only for deposition of the sample and is withdrawn by the autosampler mechanism when sample deposition has been achieved. The sample is deposited on the part 10 of the head 3 on the opposite side of the ridge 5 from the step 4. The probe 1 is dimensioned and positioned so that the step 4 is close to the slot 7 when the probe is inserted into the cuvette to minimise the escape of atomised sample through the slot 7 and thus maximise the measurement sensitivity.

An experimental probe designed for use with a Pye Unicam GF8 Electrothermal atomiser had a stem thickness of 1.5 mm, a head thickness of 0.3 mm and a ridge height of 0.7 mm. The head length was 8 mm and the ridge was spaced 4 mm from the free end of the head and was 0.5 mm thick.

FIGS. 5,6 and 7 show a cuvette 15, a probe 16, and an actuator 17 mounted in and on an atomiser for an atomic absorption spectrophotometer. The probe 16 takes the form of a probe as described with reference to FIGS. 1 and 2 and the cuvette 15 is a hollow cylindrical graphite body. The atomiser comprises a body 20 having a hinged door 21. Within the atomiser body 20 two contact jaws, one of which is shown at 22 grip each end of the cuvette 15. The jaws have electrical connection terminals, one of which is shown at 23, to which, in operation, an electrical current source is connected for passing a current through the cuvette 15 to raise its temperature to the atomisation temperature. The contact jaw 22 comprises a fixed lower portion 24 and a pivotted upper portion 25 which can be pivotted by moving a member 26 into the body 20, horizontally to the left in the embodiment shown in FIG. 7. The actuator 17, which in this embodiment is in the form of a solenoid but which may be, for example a motor and cam drive, is attached to the door 21 of the furnace by four screws 27 to 30 and the probe 16 passes through an aperture 31 in the door 21. A further aperture 32 is provided in the front of the door 11 through which a dosing tube 18 may be inserted to deposite a sample on the probe. Preferably the aperture 32 is closed when the cuvette is being heated so that the escape of protective gas is reduced. Since the cuvette 15 is normally made of carbon it is necessary to prevent rapid oxidation when it is heated to the atomising temperatures which may be in the region of 3000 degrees Celsius. Consequently it is customary to provide a flow of inert gas over and through the cuvette 15.

The door 21 is hinged along its bottom edge, being mounted between two fixed members 33 and 34 by a shaft 35 the ends of which are free to rotate in the fixed members 33 and 34. The opening and closing of the door 21 is performed by a rod 36 pivotally connected to a lug 37 on the door 21 and operated by a piston in a cylinder. Quartz windows, one of which 39 is shown are set into each side of the door 21, the quartz windows being aligned with the longitudinal axis of the tubular body 15. The door 21 is normally kept closed and only opened to replace the cuvette when it has reached the end of its life.

While the arrangement described shows an atomiser as disclosed in UK Patent Application No. 2136144A the invention is not limited to such an arrangement. A probe of the form shown in FIGS. 1 and 2 can advantageously be applied to any atomiser in which the sample is atomised off a probe. The particular shape of the head portion of the probe may also be adapted to suit the size of sample to be deposited, for example the head portion may be wider than the stem portion producing a probe which is T-shaped in plan. The probe material may be electrographite for ease of machining and may be subsequently coated with pyrolytic graphite to reduce the porosity. Alternatively a totally pyrolytic graphite or glassy carbon probes could be used but these tend to be more difficult to machine to obtain the required head profile.

I claim:

1. A graphite probe for an electrothermal atomiser, the probe comprising a stem portion and a head portion characterised in that the head portion is provided with a ridge which is dimensioned and positioned to have a heating rate similar to that of the rest of the probe head and to provide a barrier impeding the spread of liquid samples from the head to the stem when the probe head is heated within an atomiser.

2. A graphite probe as claimed in claim 1, in which the stem thickness is greater than the head thickness.

3. A graphite probe as claimed in claim 2, in which the stem thickness is greater than the head plus ridge thickness.

4. An electrothermal atomiser for a spectrophotometer, said atomiser comprising a hollow body of electrically conductive material, means for inserting a probe into the interior of the hollow body, and means for passing an electrical current through the body to heat the interior of the hollow body to a temperature which is sufficient to atomise a sample deposited on the probe wherein the probe comprises a stem portion and a head portion for receiving the sample, characterised in that the head portion is provided with a ridge which is dimensioned and positioned to have a heating rate similar to that of the rest of the probe head and to provide a barrier impeding the spread of liquid samples from the head to the stem when the probe is heated within the hollow body and that the probe insertion means is arranged to insert the probe so that the ridge is located within the hollow body.

5. An electrothermal atomiser as claimed in claim 4, in which the hollow body comprises an elongate graphite tube.

6. An electrothermal atomiser as claimed in claim 5, in which the tube is provided with a slot in its wall, and the atomiser further comprises means for inserting the probe into the tube through the slot.

7. An electrothermal atomiser as claimed in claim 6, in which the stem portion of the probe is thicker than the height of the slot, a step is formed between the head portion and the stem portion, and the means for inserting the probe is arranged to cause the step to be located adjacent to, but not touching, the exterior of the tube to substantially close the aperture formed by the slot.

* * * * *